United States Patent
Barty et al.

(10) Patent No.: US 9,476,747 B2
(45) Date of Patent: *Oct. 25, 2016

(54) ISOTOPE SPECIFIC ARBITRARY MATERIAL FLOW METER

(71) Applicant: Lawrence Livermore National Security, LLC, Livermore, CA (US)

(72) Inventors: Christopher P. J. Barty, Hayward, CA (US); John C. Post, Livermore, CA (US); Edwin Jones, Carmel Valley, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/961,807

(22) Filed: Dec. 7, 2015

(65) Prior Publication Data

US 2016/0161315 A1    Jun. 9, 2016

Related U.S. Application Data (63) Continuation of application No. 14/238,158, filed as application No. PCT/US2012/051806 on Aug. 22, (Continued)

(51) Int. Cl.
*G01N 23/10* (2006.01)
*G01V 5/00* (2006.01)

(Continued)

(52) U.S. Cl.
CPC ............ *G01F 1/7042* (2013.01); *B07C 5/346* (2013.01); *B07C 5/3416* (2013.01); *G01N 23/066* (2013.01); *G01N 23/10* (2013.01); *G01N 23/221* (2013.01); *G01V 5/0016* (2013.01); *G01V 5/0091* (2013.01); *G01N 2223/043* (2013.01); *G01N 2223/074* (2013.01);

(Continued)

(58) Field of Classification Search
CPC .. G01N 23/066; G01N 23/10; G01N 23/221; G01N 2223/043; G01N 2223/074; G01N 2223/626; G01N 2223/639; G01V 5/0016; G01V 5/0091

See application file for complete search history.

(56) References Cited

U.S. PATENT DOCUMENTS 3,780,294 A    12/1973 Sowerby
4,941,162 A    7/1990 Vartsky et al.

(Continued)

FOREIGN PATENT DOCUMENTS

WO    2005081017    9/2005
WO    2007038527    4/2007

(Continued)

OTHER PUBLICATIONS

Albert et al., "Isotope-Specific Detection of Low-Density Materials with Laser-Based Monoenergetic Gamma-Rays," Optics Letters, vol. 35, No. 3, 2010, pp. 354-356.

(Continued)

*Primary Examiner* — Thomas R Artman
(74) *Attorney, Agent, or Firm* — John P. Wooldridge (57) ABSTRACT

A laser-based mono-energetic gamma-ray source is used to provide non-destructive and non-intrusive, quantitative determination of the absolute amount of a specific isotope contained within pipe as part of a moving fluid or quasi-fluid material stream.

18 Claims, 10 Drawing Sheets

Related U.S. Application Data 2012, now Pat. No. 9,205,463, said application No. 14/238,158 is a continuation-in-part of application No. 13/552,610, filed on Jul. 18, 2012, now Pat. No. 8,934,608, which is a continuation-in-part of application No. 12/506,639, filed on Jul. 21, 2009, now Pat. No. 8,369,480, which is a continuation-in-part of application No. 11/528,182, filed on Sep. 26, 2006, now Pat. No. 7,564,241.

(60) Provisional application No. 61/509,479, filed on Jul. 19, 2011, provisional application No. 60/720,965, filed on Sep. 26, 2005, provisional application No. 61/526,109, filed on Aug. 22, 2011, provisional application No. 61/526,124, filed on Aug. 22, 2011.

(51) Int. Cl.

| | | |
|---|---|---|
| *G01F 1/704* | (2006.01) | |
| *B07C 5/34* | (2006.01) | |
| *G01N 23/221* | (2006.01) | |
| *G01N 23/06* | (2006.01) | |
| *B07C 5/346* | (2006.01) | |
| *H05G 2/00* | (2006.01) | |

(52) U.S. Cl.
CPC . *G01N 2223/626* (2013.01); *G01N 2223/639* (2013.01); *H05G 2/00* (2013.01)

(56) References Cited

U.S. PATENT DOCUMENTS

| | | | |
|---|---|---|---|
| 5,040,200 | A | 8/1991 | Ettinger et al. |
| 5,115,459 | A | 5/1992 | Bertozzi |
| 5,247,177 | A | 9/1993 | Goldberg et al. |
| 5,293,414 | A | 3/1994 | Ettinger et al. |
| 5,323,004 | A | 6/1994 | Ettinger et al. |
| 5,420,905 | A | 5/1995 | Bertozzi |
| 6,442,233 | B1 | 8/2002 | Grodzins et al. |
| 6,661,818 | B1 | 12/2003 | Feldman et al. |
| 6,684,010 | B1 | 1/2004 | Morris et al. |
| 6,687,333 | B2 | 2/2004 | Carroll et al. |
| 7,060,983 | B2 | 6/2006 | Turner |
| 7,120,226 | B2 | 10/2006 | Ledoux et al. |
| 7,564,241 | B2 | 7/2009 | Barty et al. |
| 7,596,208 | B2 | 9/2009 | Rifkin et al. |
| 7,693,262 | B2 | 4/2010 | Bertozzi et al. |
| 8,369,480 | B2 | 2/2013 | Barty |
| 8,934,608 | B2 | 1/2015 | Barty |
| 2004/0109532 | A1 | 6/2004 | Ford |
| 2005/0179911 | A1 | 8/2005 | Boomgarden et al. |
| 2006/0166144 | A1 | 7/2006 | Te Kolste et al. |
| 2006/0188060 | A1 | 8/2006 | Bertozzi et al. |
| 2006/0193433 | A1 | 8/2006 | Ledoux et al. |
| 2006/0251217 | A1 | 11/2006 | Kaertner et al. |
| 2007/0019788 | A1 | 1/2007 | Ledoux et al. |
| 2007/0263767 | A1 | 11/2007 | Brondo, Jr. |
| 2009/0147920 | A1 | 6/2009 | Barty et al. |
| 2011/0164732 | A1 | 7/2011 | Bertozzi et al. |
| 2013/0003924 | A1 | 1/2013 | Barty |
| 2013/0003935 | A1 | 1/2013 | Barty |
| 2014/0251880 | A1 | 9/2014 | Barty |

FOREIGN PATENT DOCUMENTS

| | | |
|---|---|---|
| WO | 2009086503 | 7/2009 |
| WO | 2009097052 | 8/2009 |
| WO | 2011071563 | 6/2011 |

OTHER PUBLICATIONS

Boucher et al., "Inverse compton scattering gamma ray source", Nuclear Instruments and Methods in Physics Research, A 608, 2008, pp. S54-S56.

Gibson et al., "Design and Operation of a Tunable MeV-level Compton-scattering-based x-ray source", The Americal Physical Society, Physical Review and Special Topics—Accelerators and Beams, 13, 2010, pp. 070703-1 to 070703-12.

Hagmann et al., "Transmission-based detection of nuclides with nuclear resonance fluorescence using a quasimonoenergetic photon source", J. Appl. Phys., vol. 106, 2009, pp. 1-7.

International Search Report and Written Opinion for PCT/US2012/047483 related to U.S. Appl. No. 13/552,610, 9 pages.

International Preliminary Report on Patentability for PCT/US2012/051806 related to U.S. Appl. No. 14/238,158, 5 pages.

Jovanovic et al., "High-power picosecond pulse recirculation for inverse compton scattering", Nuclear Physics B, 184, 2008, pp. 289-294.

Shverdin et al., "High-power picosecond laser pulse recirculation", Optics Letters, vol. 35, No. 13, 2010, pp. 2224-2226.

Zamfir et al., "Extreme light infrastructure: nuclear physics", Proc. of SPIE, vol. 8080, pp. 1-8.

ISOTOPE SPECIFIC ARBITRARY MATERIAL FLOW METER

CROSS-REFERENCE TO RELATED APPLICATIONS

This application is a continuation of U.S. patent application Ser. No. 14/238,158 titled "ISOTOPE SPECIFIC ARBITRARY MATERIAL SORTER" filed May 1, 2014, incorporated herein by reference, which is a 371 of International Application Number PCT/US12/51806, filed Aug. 22, 2012, incorporated herein by reference, which application claims priority to U.S. Provisional No. 61/526,109, titled "Isotope Specific Arbitrary Material Sorter," filed Aug. 22, 2011, incorporated herein by reference and to U.S. Provisional No. 61/526,124, titled "Isotope Specific Material Flow Meter," filed Aug. 22, 2011, incorporated herein by reference. U.S. patent application Ser. No. 14/238,158 is a continuation-in-part of U.S. patent application Ser. No. 13/552,610, now U.S. Pat. No. 8,934,608, titled "High Flux, Narrow Bandwidth Compton Light Sources Via Extended Laser-Electron Interactions," filed Jul. 18, 2012, incorporated herein by reference. U.S. patent application Ser. No. 13/552,610 claims priority to U.S. Provisional Patent Application No. 61/509,479, titled. "High Flux, Narrow Bandwidth Compton Light Sources Via Asymmetrical Laser-Electron Interactions," filed Jul. 19, 2011, incorporated herein by reference. U.S. patent application Ser. No. 13/552,610 is a continuation-in-part (CIP) of U.S. patent application Ser. No. 12/506,639, now U.S. Pat. No. 8,369,480, titled "Dual Isotope Notch Observer for Isotope Identification, Assay and Imaging with Mono-Energetic Gamma-Ray Sources" filed Jul. 21, 2009, incorporated herein by reference. U.S. patent application Ser. No. 12/506,639 is a UP of U.S. patent application Ser. No. 11/528,182, now U.S. Pat. No. 7,564,241, titled "isotopic Imaging Via Nuclear Resonance Fluorescence with Laser-Based Thomson Radiation" filed Sep. 26, 2006, incorporated herein by reference. U.S. patent application Ser. No. 11/528,182 claims priority to U.S. Provisional Patent Application No. 60/720,965 filed Sep. 26, 2005, incorporated herein by reference.

STATEMENT REGARDING FEDERALLY SPONSORED RESEARCH OR DEVELOPMENT

The United States Government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND OF THE INVENTION

1. Field of the Invention

The present invention relates to Compton light sources, and more specifically, it relates to the use of ultra-narrow bandwidth (10E-3 or lower) and high beam flux quasi-mono-energetic x-rays and gamma rays for determining isotopic content of materials.

2. Description of Related Art

Mono-Energetic Gamma-rays (MEGa-rays) can be used to efficiently excite nuclear resonances (so called Nuclear Resonance Fluorescence or NRF) that are unique isotopic signatures of all materials. By monitoring the absorption of resonant photons from a MEGa-ray beam, one may rapidly determine the presence or absence of specific isotopes in an object and with the appropriate detector one may also determine the absolute amount of that isotope present. Furthermore, because most NRF resonances are in the 1 MeV to 3 MeV spectral range, this evaluation can be accomplished on thick (meter scale) objects if sufficiently high flux MEGa-ray beams are employed. As discussed infra, beams of mono-energetic gamma-rays can be produced by Thomson (or more precisely Compton) scattering of short duration laser pulses off of relativistic bunches of electrons. The output of these laser-based MEGa-ray sources are collimated, directional, polarized, extremely bright and tunable via adjustment of either the laser color or the electron beam energy. As discussed infra, the detection of the narrow band resonant gamma-ray absorption can be accomplished with a dual isotope notch observation (DINO) detector.

U.S. Pat. No. 7,564,241, titled "Isotopic Imaging Via Nuclear Resonance Fluorescence with Laser-Based Thomson Radiation," filed Sep. 26, 2006, incorporated herein by reference, teaches laser-based gamma-ray sources based on Compton scattering and further teaches their use for the isotope-specific detection of materials. U.S. patent application Ser. No. 12/506,639, titled "Dual isotope Notch Observer for Isotope Identification, Assay and Imaging with Mono-Energetic Gamma-Ray Sources," filed Jul. 21, 2009, incorporated herein by reference, teaches a mono-energetic gamma-ray detection technology that can be used in conjunction with a laser-based gamma-ray source to accurately detect and assay the isotopic content of a material. This technology is sometimes referred to as the Dual Isotope Notch Detector (DINO).

U.S. patent application Ser. No. 13/552,610, now, U.S. Pat. No. 8,934,608, titled "High Flux, Narrow Bandwidth Compton Light Sources Via Extended Laser-Electron Interactions," filed Jul. 18, 2012, incorporated herein by reference teaches means for producing high flux beams of bright, tunable, polarized quasi-monoenergetic x-rays or gamma-rays via laser-Compton scattering x-ray or gamma-ray. An electron source generates a train of spaced electron bunches and an RF linear accelerator accelerated the electron bunches into a laser-electron beam interaction region. The transit time of each of the accelerated electron bunches through the laser-electron beam interaction region is both greater than the duration of the accelerated electron bunch and greater than the spacing between electron hunches. A laser system is adapted to produce a laser pulse having a duration at least as long as a transit time of the laser pulse through the laser-electron beam interaction region. The laser system is arranged so that the laser pulse traverses the laser-electron beam interaction region to interact with all of the accelerated electron bunches of the train. In some embodiments, the duration of the laser pulse is substantially equal to at least a total length of the train of spaced electron bunches so that a single pass of the laser pulse through the laser-electron beam interaction region interacts with all of the accelerated electron bunches of the train. In other embodiments, the duration of the laser pulse is substantially equal to a sub-multiple of a total length of the train of spaced electron bunches. The laser system is arranged to recirculate the laser pulse through the laser-electron beam interaction region for a predetermined number of passes equal to an inverse of the sub-multiple. The spacing frequency of the electron bunches can the same as or correlated to the RF frequency of the RF linear accelerator so that an electron bunch is present for every cycle of said RF frequency.

It is desirable to utilize ultra-narrow bandwidth (10E-3 or lower) and high beam flux quasi-mono-energetic x-rays and gamma rays to determine the flow rate and/or sort materials according to isotopic content.

SUMMARY OF THE INVENTION

Embodiments of the present invention use a Laser-based mono-energetic gamma-ray source to provide, non-destructive and non-intrusive, quantitative determination of the absolute amount of a specific isotope contained within pipe as part of a moving fluid or quasi-fluid material stream. Other techniques for providing relative movement between fluid or quasi-fluid material and a MEGa-ray beam will be apparent to those skilled in the art based on the teachings herein.

The device provides instantaneous information regarding the flow rate of the particular isotope and can be used to determine the total of that isotope contained within a fix volume of the fluid that has passed the measurement point. The pipe containing the moving fluid is configured to pass in front of a MEGa-ray beam which spans the width of the pipe and has been tuned to the nuclear resonance fluorescence transition of the desired isotope in material stream. As the material containing the desired isotope traverses the beam a reduction in the transmitted MEGa-ray beam occurs. This reduction is quantitatively monitored by an appropriate nuclear resonance fluorescence detector and this information is in turn used to determine the mass amount of that isotope that has passed the inspection point in a fixed time.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Embodiments of the present invention provide new devices, based on the teachings of the incorporated descriptions, that can be used to sort and/or determine isotopic content and concentration of inhomogeneous bulk materials according to the specific elements and isotopes that they may contain. The present invention has a variety of uses, including sorting of nuclear fuel pellets in hybrid fusion-fission reactors and for sorting bulk materials extracted during mining processes prior to the materials being crushed and chemically (or otherwise) separated. Based on the teachings of this disclosure, those skilled in the art will be able to envision a number of other applications in which bulk, inhomogeneous materials could be sorted either by elemental or isotopic content.

Figure 1:
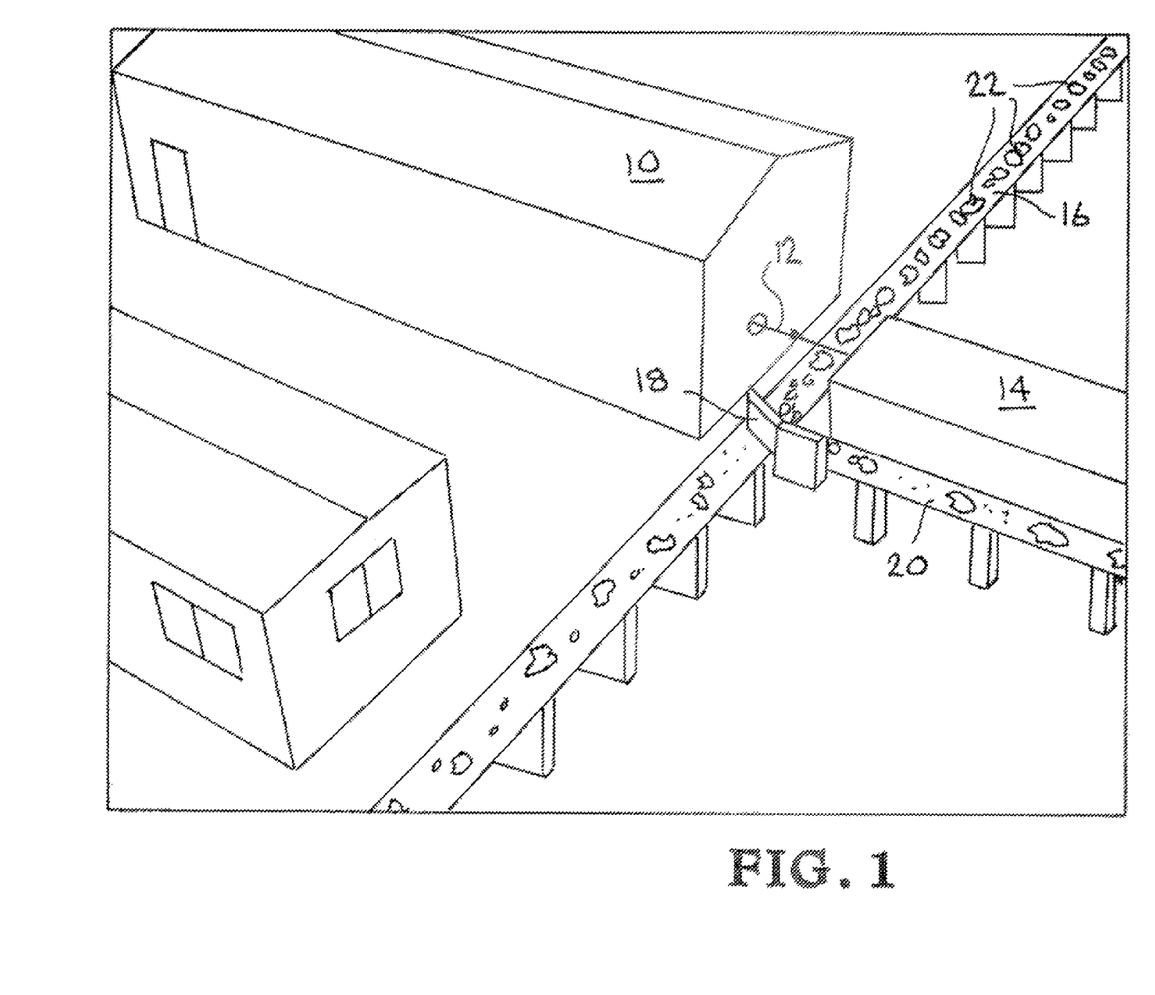
FIG. 1 illustrates an embodiment of the present isotope-specific material sorter.

As exemplified in FIG. 1, the present isotope-specific material sorter consists of three basic components, namely: the MEGa-ray source (located in enclosure 10) to provide a beam 12 tuned to resonance of a material of interest, MEGa-ray absorption detectors 14 such as DINO detectors, a main conveyor system 16 and a diverter 18 which moves specific batches of material off of the main conveyor system into a collection bin (not shown) or onto a secondary conveyor system 20 for accumulation.

In operation, one would place on the main conveyor system 16 the materials 22 to be sorted, e.g., uncrushed rock and debris from a strip mining operation. This material would be passed between the MEGa-ray beam 12 and the DINO detector 14, which has been set up to detect a specific isotope and thus element. (Multiple DINO detectors can be used to detect multiple isotopes.) In doing so, each object on the belt would be evaluated for the presence or absence of the specific desired isotope or element anywhere within that object. With an optimized MEGa-ray source and DINO detector, it is possible to detect the presence or absence of a particular isotope in a time period of the order of milliseconds. Each time this detector arrangement senses the presence of a significant amount of the desired material, a signal is sent to the downstream diverter 18 and when the material arrives at that location, it is removed from the main conveyor system 16 and into a collection bin or onto the secondary conveyor system 20 for collection downstream. For mining operations this would greatly reduce the processing costs for given materials. The material sorter is isotope specific and thus element specific and performs very rapidly. It is able to determine the presence of materials contained within the interior of large objects (large rocks in the case of the mining example). In principle, quantitative information regarding the total amount of a desired isotope or element that might be present in the object can also be obtained with longer object dwell time in the beam.

As briefly discussed, embodiments of the present sorter may be used in a variety of applications, including to sort nuclear fuel pebbles in a hybrid fusion-fission Laser Inertial Fusion Energy (LIFE) reactor. This sorting enables separation of pebbles containing differing concentrations of fissionable materials so that they may be optimally re-inserted into the reactor for burn up. Further applications include sorting of bulk electronics waste for valuable materials and sorting of bulk metallic waste for valuable materials. Further, this invention can be used on streams of objects that contain finite size objects of a non-uniform nature or composition.

Other embodiments of the invention non-destructively and non-intrusively determine the absolute amount of a specific Isotope in an arbitrary and potentially inhomogeneous fluid stream. The origin of this concept arose from discussions with researchers associated with the Hanford Nuclear facility and the planned waste materials vitrification plant at Hanford. (Vitrification is the transformation of a substance into a glass. In a wider sense, the embedding of material in a glassy matrix is also called vitrification. An important application is the vitrification of radioactive waste to obtain a stable compound that is suitable for ultimate disposal.) At the Hanford vitrification plant the mixed waste material from the Hanford storage tanks enters the plant via a three-inch diameter pipe. Output from these pipes fills the 20-foot-tall vitrification containers. The composition of the material within the container is estimated statistically based on chemical analysis of small, random samples of the fluid stream. This method is both time consuming, expensive and potentially highly inaccurate. There currently is no non-destructive and non-intrusive method for determining the contents of the waste streams. One can envision a number of other applications in which the non-destructive and non-intrusive measurement of a specific isotope or element in a complex fluid stream would be of importance.

Figure 2A:
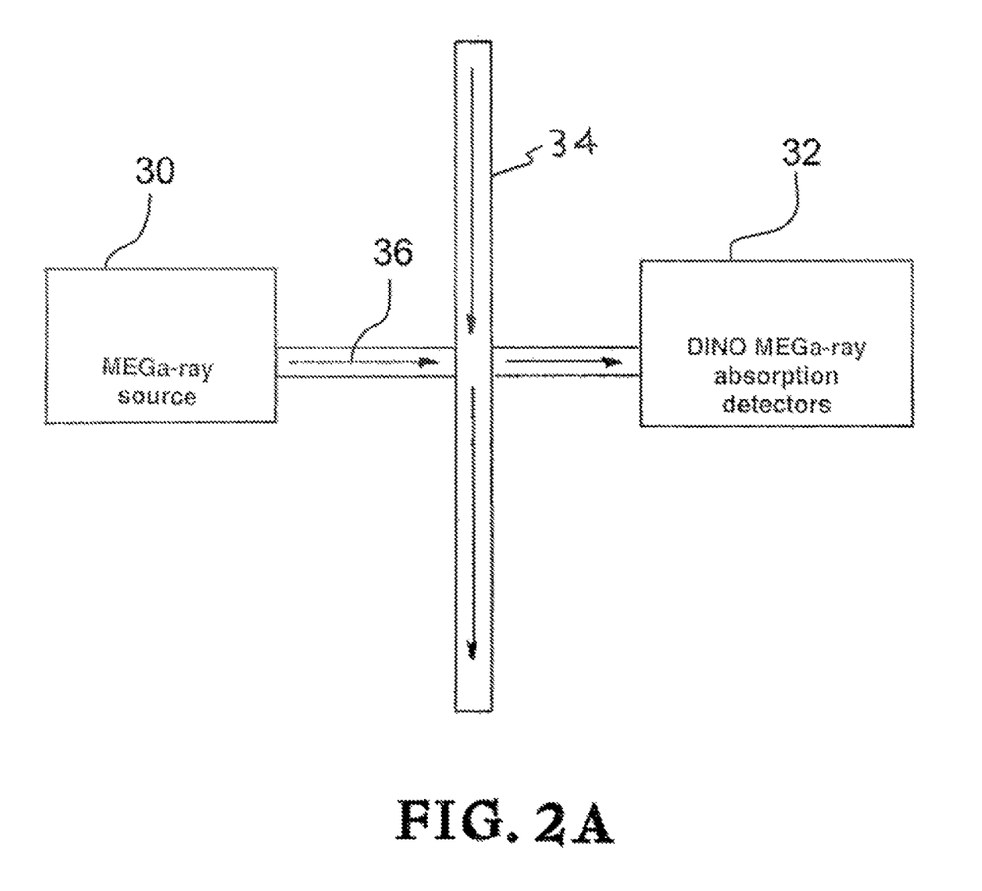
FIG. 2A illustrates an embodiment of the present the isotope-specific material flow meter.
Figure 2B:
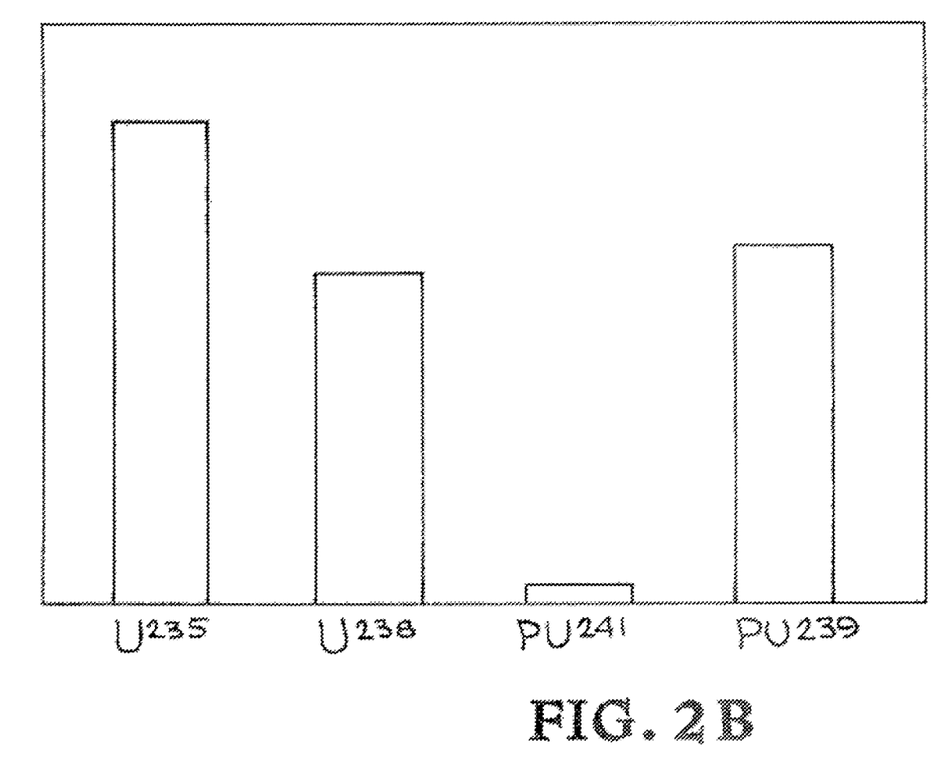
FIG. 2B shows an output reading from the flow meter of FIG. 2A.

As exemplified in FIG. 2A, the isotope-specific material flow meter invention consists of two basic components namely: the MEGa-ray source (located in enclosure 30) tuned to resonance of a material of interest and one or more computer controlled, DINO MEGa-ray absorption detectors 32. Exemplary MEGa-ray sources are described in U.S. patent application Ser. No. 11/528,182, titled "Isotopic Imaging Via Nuclear Resonance Fluorescence with Laser-Based Thomson Radiation," filed Sep. 26, 2006, incorporated herein by reference. Further exemplary MEGa-ray sources are briefly described infra and are more specifically described in U.S. patent application Ser. No. 13/552,610, titled "High Flux, Narrow Bandwidth Compton Light Sources Via Extended Laser-Electron Interactions," filed Jul. 18, 2012, incorporated herein by reference. Exemplary DINO MEGa-ray absorption, detectors are briefly described infra and are more specifically described in U.S. patent application Ser. No. 12/506,639, titled "Dual Isotope Notch Observer for Isotope Identification, Assay and Imaging with Mono-Energetic Gamma-Ray Sources", filed Jul. 21, 2009, incorporated herein by reference.

Referring still to FIG. 2A, in operation, a pipe 34 is arranged so that fluid contained in the pipe passes between the MEGa-ray bean 36 and the DINO detector(s) 32. The MEGa-ray beam is tuned to the NRF resonance of the desired isotope, e.g., U235, and the beam output is adjusted in size to subtend the full width of the fluid stream contained within the pipe. The DINO detector is placed on the other side of the pipe and consists of detection foils that are sized to interact with the full MEGa-ray beam after it has passed through the pipe. The DINO foils are composed of isotopes of the material in the pipe that is to be measured, e.g., 235U and 238U. As the material flows between the MEGa-ray beam and the DINO detector, the presence of the resonant isotope causes attenuation on the MEGa-ray beam. The quantitative amount of this attenuation is measured by the difference and/or ratio of the scattered signal from the DINO detector foils. With a MEGa-ray beam of sufficient flux, it is possible to record the attenuation as a function of time. With knowledge of the overall material flow rate in the pipe it is then possible to determine the flow rate of the isotope within the pipe and the total amount of the specific isotope that has passed the measurement point in a given time. This arrangement provides a number of advantages. It is isotope specific and thus element specific. The quantitative potential extends to parts per million. The technique is non-destructive to the pipe and the fluid and is non-intrusive to the fluid flow. Physical removal of material from the pipe or the fluid flow is not required. This system is easily adaptable to multiple isotope measurements by changing the MEGa-ray photon energy and the DINO detection foils. The invention has multiple applications, including control and monitoring of process flow streams in chemical plants, e.g., measurement of one chemical constituent via measurement of the passage of specific isotopes within the stream. Chemicals could be tagged with a given isotope and monitored. Another application provides measurement of fluid flow in biological and medical systems, e.g., it can be used to monitor the flow rate of oxygen in the blood stream via measurement of the passage of specific oxygen isotopes. Drug delivery could be monitored via tagging with specific isotopes. Note that the isotopes could be long lived and non-radioactive. Further, this invention is useful for diagnosing material streams of non-uniform and varying composition.

Figure 3:
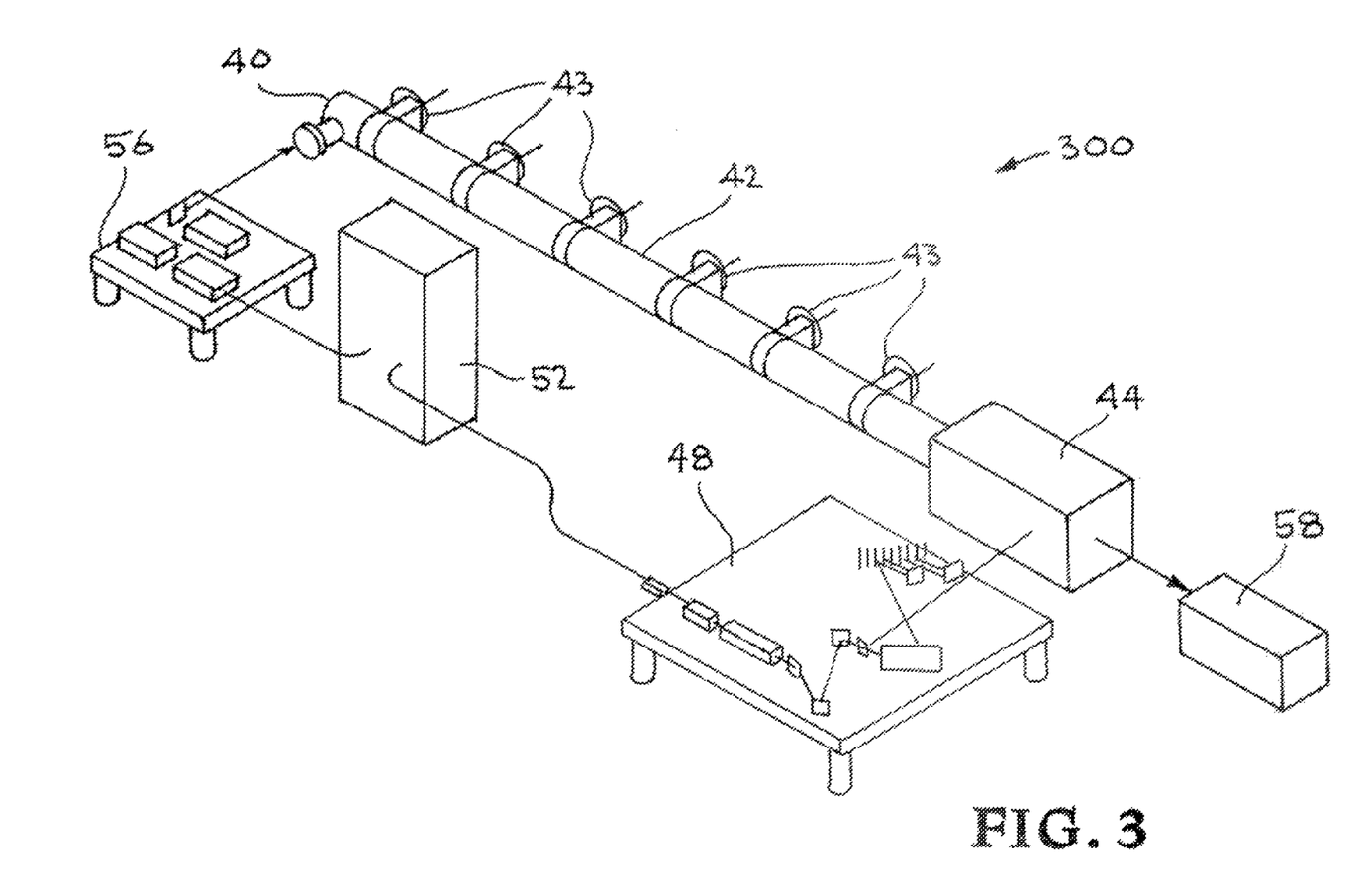
FIG. 3 shows a more detailed representation of a Nuclear Resonance Fluorescence (NRF) based interrogation system of the present invention, including the main components of the monochromatic, tunable inverse Compton x/gamma-ray source.

Exemplary MEGa-ray sources are described in U.S. patent application Ser. No. 11/528,182, now U.S. Pat. No. 7,564,241, titled "Isotopic Imaging Via Nuclear Resonance Fluorescence with Laser-Based Thomson Radiation," filed Sep. 26, 2006, incorporated herein by reference. FIG. 3 shows a more detailed representation of the system, generally designated as reference numeral 300, of the present invention, and includes an RF photocathode gun 40, a linear accelerator 42, an interaction region 44, an interaction laser system 48, a fiber optics rack 52, a photo-cathode driver system 56, and the detector configuration 58, as shown and discussed above in FIG. 1. Each of the sub-assemblies are discussed below in greater detail.

The electron source of the present invention utilizes a 1.6 cell RF photo-cathode gun based design known by those of ordinary skill in the art. The RF gun 40, as shown in FIG. 3, designed and built in collaboration with UCLA is an improved apparatus because of symmetrization and suppression of a parasitic field mode. Frequency tuners in previous versions of such a gun design caused breakdowns at field strengths above 100 MV/m. These tuners have been removed, and are replaced by symmetrizing slots (not shown) identical to the RF input and vacuum pump-out slots. This measure allows peak field strengths of up to about 120 MV/m, necessary for high-brightness performance. Additional symmetrizing measures include the removal of off-axis laser input ports (not shown), and the inclusion of a corrector coil (not shown), which compensates for dipole and quadrupole moments of the main focusing solenoid.

The gun 40, as shown in FIG. 3, as an RF system that includes two coupled cavities, has two resonant modes, the accelerating, or $\pi$-mode, and the parasitic 0-mode. The excitation of the 0-mode can have a detrimental effect on the emittance and energy spread of the generated electron beam. The present invention provides a solution to this problem by increasing the frequency separation between the 0 and $\pi$-modes, thereby decreasing the amount of 0-mode excitation that occurs in normal operation, which has increased the mode separation from about 3.5 MHz to about 12 MHz. Such a design has been modeled with an emittance as low as about 0.6 mm-mrad rms for a 1 nC bunch.

Embodiments of the present invention utilize a linear accelerator (linac). An older version operating in the s-band is depicted in FIG. 3 as reference numeral 42 and includes quadrupoles 43 located between accelerating sections in order to transport and accelerate the low emittance electron bunch produced by the gun without significant degradation in beam quality. A new version, operating in the x-band, is briefly described below and in U.S. patent application Ser. No. 13/552,610, titled "High Flux, Narrow Bandwidth Compton Light Sources Via Extended Laser-Electron Interactions," filed Jul. 18, 2012, incorporated, herein by reference.

Figure 4:
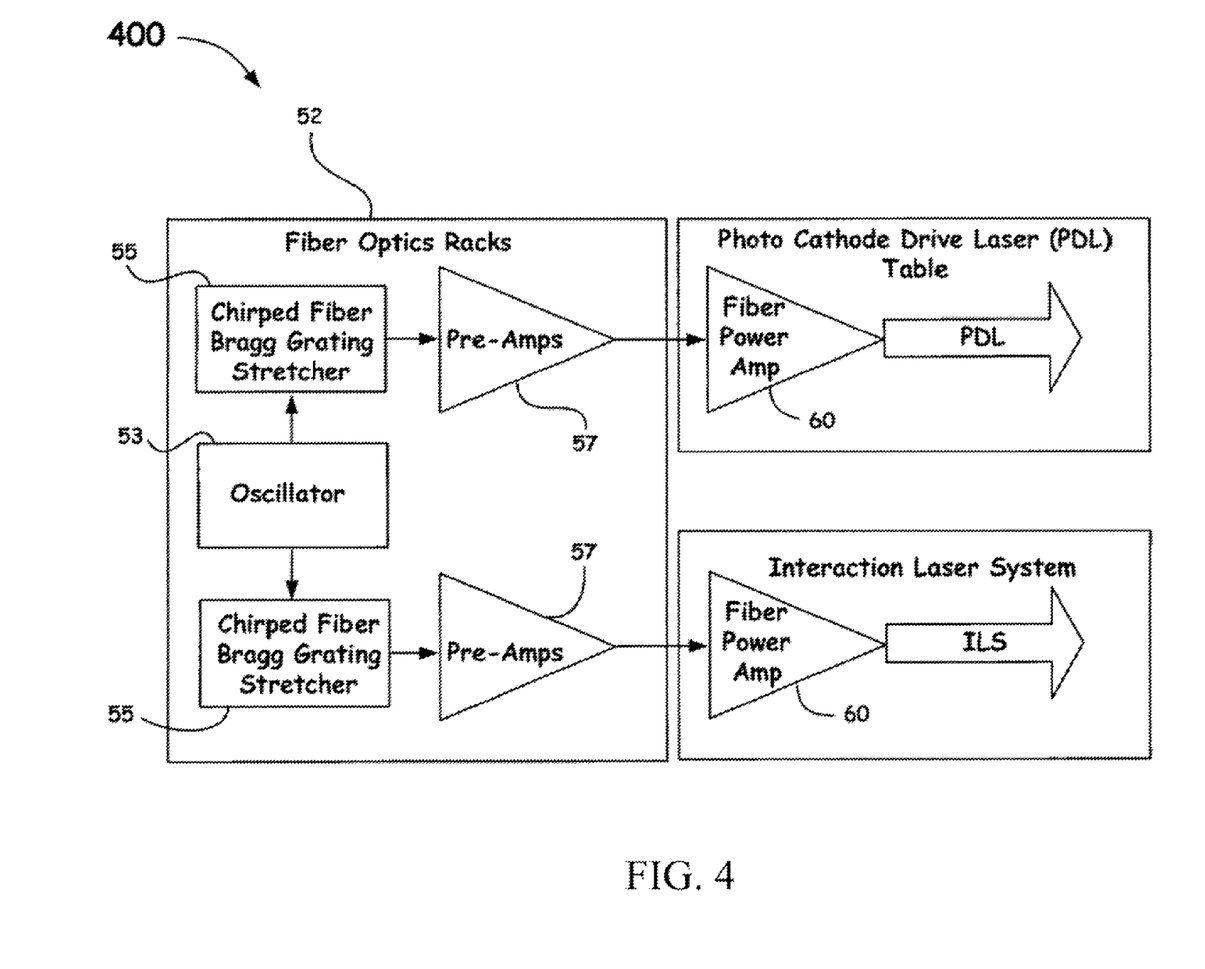
FIG. 4 shows a schematic of the Seed Laser System (SLS).

The Seed Laser System (SLS) is preferably based on optical fiber technologies to make it reliable, robust, and compact. The SLS, as shown in FIG. 4 generally designated by reference 400, is physically divided into three sections, as follows:

A rack-mounted fiber optics unit, 52 as shown in FIG. 3 and in FIG. 4, includes:

A passively mode-locked oscillator 53 that can generate a train of 150 fs pulses locked to a frequency of 40.7785 MHz±1 Hz. The pulse spectrum spans 1040 nm through 1070 nm so this single oscillator can seed both the PDL and the ILS.

A pair 55 of chirped fiber Bragg gratings (CFBG's): one to stretch the PDL pulse train and another to stretch the interaction laser (ILS) train. The CFBG's are double-passed to obtain a total stretch of 6 ns.

Yb-doped fiber pre-amplifiers 57, often six Yb-doped fiber pre-amplifiers: three for the PDL line and three for the ILS line. These raise the pulse energy in each line from roughly about 0.1 nJ at 40 MHz to about 10 nJ at 2 kHz. Each pre-amplifier also contains an isolator (not shown), an acousto-optic modulator (not shown) to clean the pulses in the time domain, and an optical tap (not shown) for monitoring purposes. A pair of tabletop high-energy amplifiers 60: one for the PDL line and one for the ILS line. The amplifiers often include, but are not limited to:

A section of Yb-doped fiber to convert the output received from the fiber optics rack (e.g., about 10 nJ pulses plus 300 W of pump power at 976 nm) up to about 1 µJ pulses. The conversion is delayed to the table-tops to reduce the non-linear effects that can accrue during transport from the rack to the tables. A final amplifier section can raise the pulse energy up to about 1 mJ having phase errors in the spectral components to less than about π/4.

A control and analysis means (not shown), such as, but not limited to, a desktop or laptop computer is often arranged to monitor and control the outputs of the pre-amplifier stages and final amplifier to ensure reliable day-to-day operation and to intervene if one or more of the stages show signs of failure. Such an analysis means can also monitor the frequency and phase of the locking circuitry, and make minor adjustments to beam pointing to adjust for anticipated thermal drifts.

It is to be appreciated that the final amplifier fiber ultimately limits the achievable pulse energy because of inherent nonlinearities and damage threshold. Accordingly, while various amplifier fibers may be incorporated, most often a 40 µm single-mode, single-polarization fiber from Crystal Fibre, or a 30 µm fiber from LIEKKI is integrated into the present invention to provide the desired beam quality and polarization extinction ratio.

A Photocathode Drive Laser (PDL) 56, as shown in FIG. 3, of the present invention generates the photoinjector drive pulse for the photocathode 40 in the linac photoinjector. The system has been designed to deliver a "beer-can" shaped pulse with energy of up to about 100 µJ at 261.75 nm. The "beer-can" shape (a flattop in both space and time) is 10 ps at FWHM, with ~800 fs rise and fall times. The spot-size diameter of the beam measures 2 mm.

Figure 5:
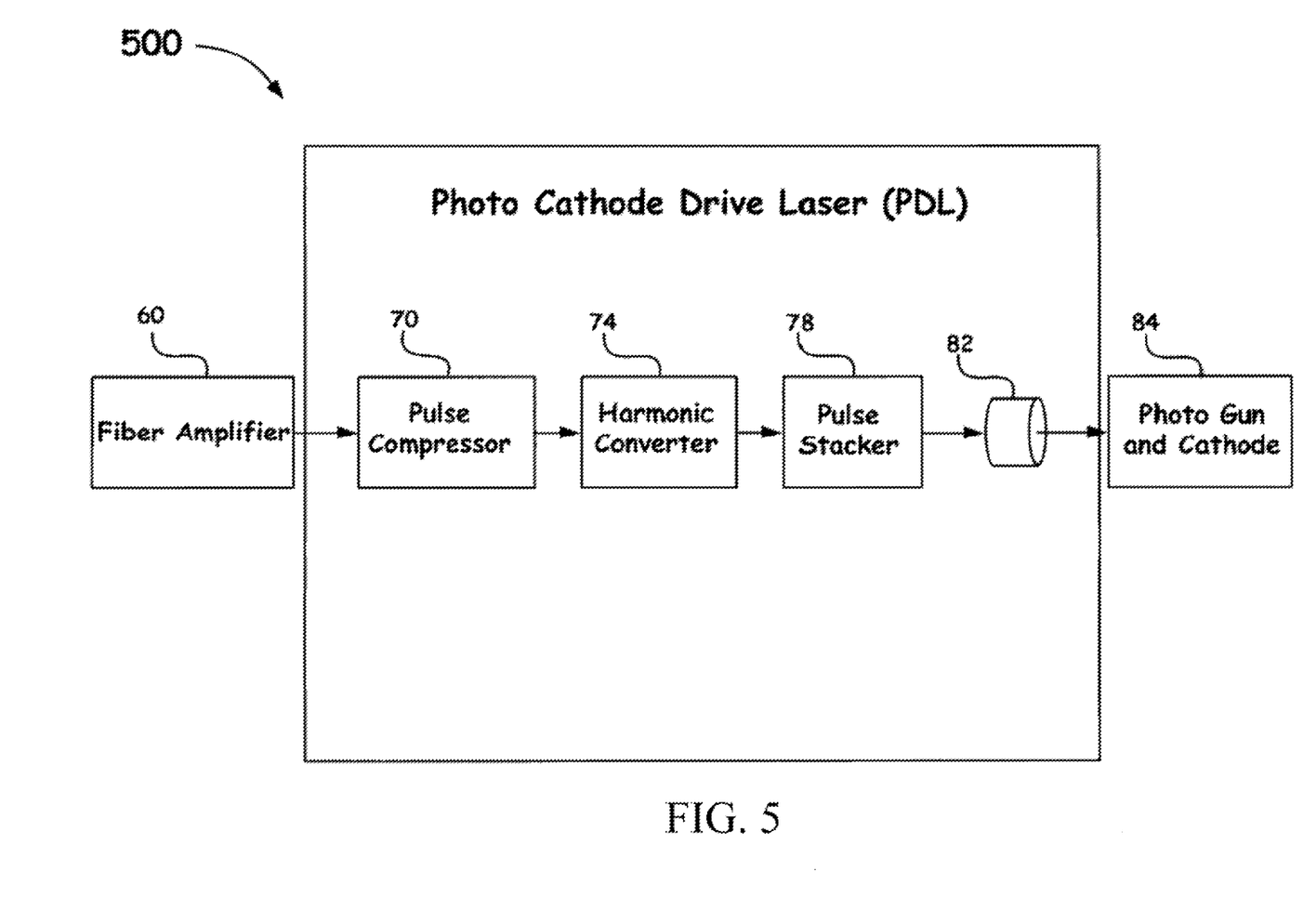
FIG. 5 shows a schematic of the Photocathode Drive Laser (PDL).

The PDL system, generally designated by reference numeral 500, as shown by the schematic representation in FIG. 5, often includes 4 main components: a pulse compressor 70, a harmonic conversion stage 74, a pulse stacker 78, which temporally shapes the UV pulse, and a custom designed phase mask optic 82, which spatially reshapes the Gaussian UV pulse to a substantially flattop profile. An exemplary input to the PDL, generated by the SLS system, upon amplification by Fiber Amplifier 60, is a ~500 µJ pulse at 1047 nm with a ~10 nm bandwidth stretched to ~4.8 ns FWHM.

Compressor 70 compensates for the group delay dispersion (GDD) and third-order dispersion (TOD) introduced in the SLS system while recompressing the input pulse from about 4.8 ns to about 250 fs FWHM. The preferred design is a quad-pass pulse compressor, having a resultant GDD=−3.4×$10^8$ $fs^2$, and TOD=4.7×$10^9$ $fs^3$, and often includes one 1740 groves/mm grating, 1 horizontal roof mirror, 1 large vertical roof mirror, and 1 small vertical roof mirror so as to achieve a dispersion of about 600 ps/nm.

In a further method of the present invention, the compressed pulse is frequency-quadrupled from 1047 nm to 261.75 nm in harmonic converter 74, as shown in FIG. 5. Harmonic conversion occurs in two steps. First, the pulse is frequency-doubled to 523.5 nm with, for example, a BBO crystal in the Type I configuration (crystal cut angle=23.2, crystal thickness, ~600 µm). The residual 1047 nm beam is then filtered out using a dichroic mirror. The up-converted beam can then be frequency Type I frequency-doubled from 523.5 nm to 261.75 nm by a different BBO crystal. The conversion efficiency from 2ω to 4ω is limited by the 2-photon nonlinear absorption of the UV radiation in the BBO crystal. This constraint is partly overcame by using two 2ω to 4ω doubling crystals. The first BBO crystal partially depletes the green (523.5 nm) pump. The generated UV beam is then separated out with a dichroic mirror; the residual green beam is sent to a second BBO crystal. The two generated UV beans are later recombined in the pulse stacker. The BBO crystals are chosen thin enough to minimize 2-photon absorption. The first 2ω to 4ω BBO crystal is ~200 µm thick and the second BBO crystal is ~400 µm thick.

A pulse stacker 78, as shown in FIG. 5, of the present invention is often a Michelson-based ultrafast pulse multiplexing device having nearly 100% throughput and designed for high energy shaped pulse generation. The pulse stacker generates a train of replicas of the input pulse delayed with respect to each other with femtosecond precision. Half of the produced pulses are s-polarized and half are p-polarized. Appropriate setting of the interferometer arm lengths results in many different output pulse formats. The designed pulse stacker can include 4 stages and two input ports (for the two generated UV beams), capable of stacking up to 32 pulses. To create the optimal photo-injection pulse, the two UV input pulses are initially temporally stretched to ~400 fs and then multiplexed with the pulse stacker to create a train of orthogonally polarized pulses spaced by 280 fs, which corresponds to a temporal flattop pulse with 10 ps duration and 1 ps rise time having some minimal temporal modulation caused by pulse interference.

To maximize beam throughput and minimize the footprint of the pulse stretcher, a four-prism set-up can often be utilized. The beam is incident on each of the fused silica prisms at Brewster's angle. A prism pair separation of 50 cm stretches a 250 fs transform-limited pulse to 1.2 ps FWHM.

A custom-designed phase mask optic 82, as shown in FIG. 5, reshapes the input Gaussian pulse to a flattop spatial profile. The optic imparts a spatial phase to the UV beam to produce a flattop pulse in the Fourier plane. The beam shape is preserved by imaging the Fourier plane to the photo-cathode 84, as shown in FIG. 5.

Resizing of the beam waist at the different stages of the PDL system is achieved with an off-axis beam (de-)expander. The beam expander is preferably a concave (R=75 cm) and a convex (R=−50 cm) mirror placed at a slight angle (~0.5 deg) with respect to each other. This design eliminates any astigmatism introduced by a conventional on-axis mirror expander.

The designed PDL system can be made to fit on a 2'×8' optical board, so as to be placed next to the linac photoinjector approximately 2 m from the photocathode. The beam then can be imaged from the optical board layout to the photocathode.

The purpose of the Interaction laser System (ILS) 48, as shown in FIG. 3, is to deliver Joule-class 355-nm pulses (the third harmonic of Nd:YAG) to the interaction region 44 at up to about a 10-Hz rate, synchronous with the photoinjector and linac 42. While Nd;YAG is a beneficial laser and amplifier material, other laser materials, such as, but not limited to, Yb:YAG, Nd:YLF, Neodymium(Nd)-doped glass, Yb:YAG, Ti:Sapphire, Yb:glass, KGW, KYW, YLF, S-FAP, YALO, YCOB, Cr:forsterite, and GdCOB and associated amplifying hardware can also be utilized in the present invention without departing from the spirit and scope of the present invention.

It is to be appreciated that the nominally picosecond duration achievable with Nd:YAG (limited by the available gain bandwidth) includes a seed source phase locked to the photo-cathode drive laser (PDL) 56, as shown in FIG. 3, a multi-head Nd:YAG power amplifier, and a unique hyper-dispersion pulse compressor.

The seed laser system includes a fiber-based system designed to deliver 1064-nm seed pulses temporally stretched to 6-ns duration in a double-passed chirped-fiber Bragg grating. These pulses are amplified to the mJ level in a multi-stage fiber amplifier, at which point they are available to be injected in the ILS power amplifier. Though amplification in Nd:YAG will naturally limit the bandwidth of the energetic output pulses, the ILS seed pulses are amplified with a 1 to 2 nm FWHM bandwidth in order to spectrally fill the available gain spectrum.

The nominally 6-ns long 1064-nm pulses supplied by one arm of the SLS are quite similar to the seed pulses used in commercial Q-Switched Nd:YAG lasers. Such lasers are typically limited to less than a handful of longitudinal modes as opposed to the wide-spectrum chirped pulses we will use. As long as the bandwidth of the seed pulses is on the order of the available gain bandwidth, stock Nd:YAG amplifiers from a commercial vendor can be used to boost the mJ-level output of the SLS fiber amplifiers to the Joule-level. This is indeed the path being taken for the ILS amplifier. The design can be arranged with three commercial flashlamp-pumped Nd:YAG laser heads: a 4-pass 6-mm and two 12-mm single-pass rods in a birefringence compensating configuration, with an estimated 3-J output energy.

Chirped-pulse amplification in Nd:YAG with nanometer band widths requires a cascaded-grating "hyper-dispersion" architecture to provide the necessary dispersion (~3000 ps/nm) in a compact meter-scale compressor. The design, as disclosed herein, uses four multi-layer diffraction (MLD) diffraction gratings in a double-pass configuration (eight grating reflections in total), however by utilizing appropriate folding of the beam path only a single large-area (35-cm× 15-cm, 1740 g/mm) grating is required. A detailed discussion of related hyper dispersion architectures and methods can be found in U.S. application Ser. No. 11/166,988, filed Jun. 23, 2005, titled "Hyper Dispersion Pulse Compressor For Chirped Pulse Amplification Systems" by Barty, and assigned to the assignee of the present invention, the disclosure of which is herein incorporated by reference in its entirety.

Further exemplary MEGa-ray sources are briefly described infra and are more specifically described in U.S. patent application Ser. No. 13/552,610, titled "High Flux, Narrow Bandwidth Compton Light Sources Via Extended Laser-Electron Interactions," filed Jul. 18, 2012, incorporated herein by reference.

The new pulse format and interaction geometry produces both ultra-narrow bandwidth (10E-3 or lower) and high beam flux quasi-mono-energetic x-rays and gamma-rays. The basic idea has three components: 1) distribute the charge of the electron bunch over many smaller charge bunches, 2) increase the focal spot size of the interaction so that the transit time of the electron bunch through the interaction region is significantly longer than the duration of the electron bunch and significantly longer than the spacing between successive electron bunches and 3) use a long duration laser pulse whose pulse duration is chosen to be as long or longer than the transit time of the laser through, the interaction region. In this way one laser pulse can interact with many (e.g., 100 or more) electron bunches at one time thus producing a high flux (in fact higher than the conventional geometry if the laser energy is adjusted correctly). Furthermore, the long duration laser pulse has narrower bandwidth than short duration laser pulses thus the gamma-ray bandwidth contribution from the laser is reduced (typically by a 1000 fold). Furthermore, because the bunch charge of the electrons is smaller, the space charge dependent energy dispersion of the bunch is smaller and the energy spread is smaller, thus the e-beam contribution to the gamma-ray bandwidth is reduced (typically by a factor of 10 or more). Further, because the bunch charge is smaller, the quality of the electron beam is higher, i.e., the emittance which is typically proportional to square root of charge is lower. Lower emittance beams can be focused to a given spot size for a longer length. This leads to a longer and more collimated laser-electron beam interaction which in turn reduces the focusing contribution to gamma-ray bandwidth (typically another factor of 10). Finally, because the electron beam and laser foci are relatively large and the laser pulse duration is relatively long, the intensity of the laser pulse in the interaction region is reduced (100 fold or more) and thus non-linear effects which tend to broaden the bandwidth of gamma-ray sources are also reduced dramatically. One might not need to focus the electron beam at all out of the accelerator, only the laser beam. In some x-band structures the beam diameter can be 100 microns right out of the device and this is approximately the laser diameter in the focal region. Not having to focus the electron beam means that there is no need for focusing quadrupoles, thus saving space and complexity.

Figure 6:
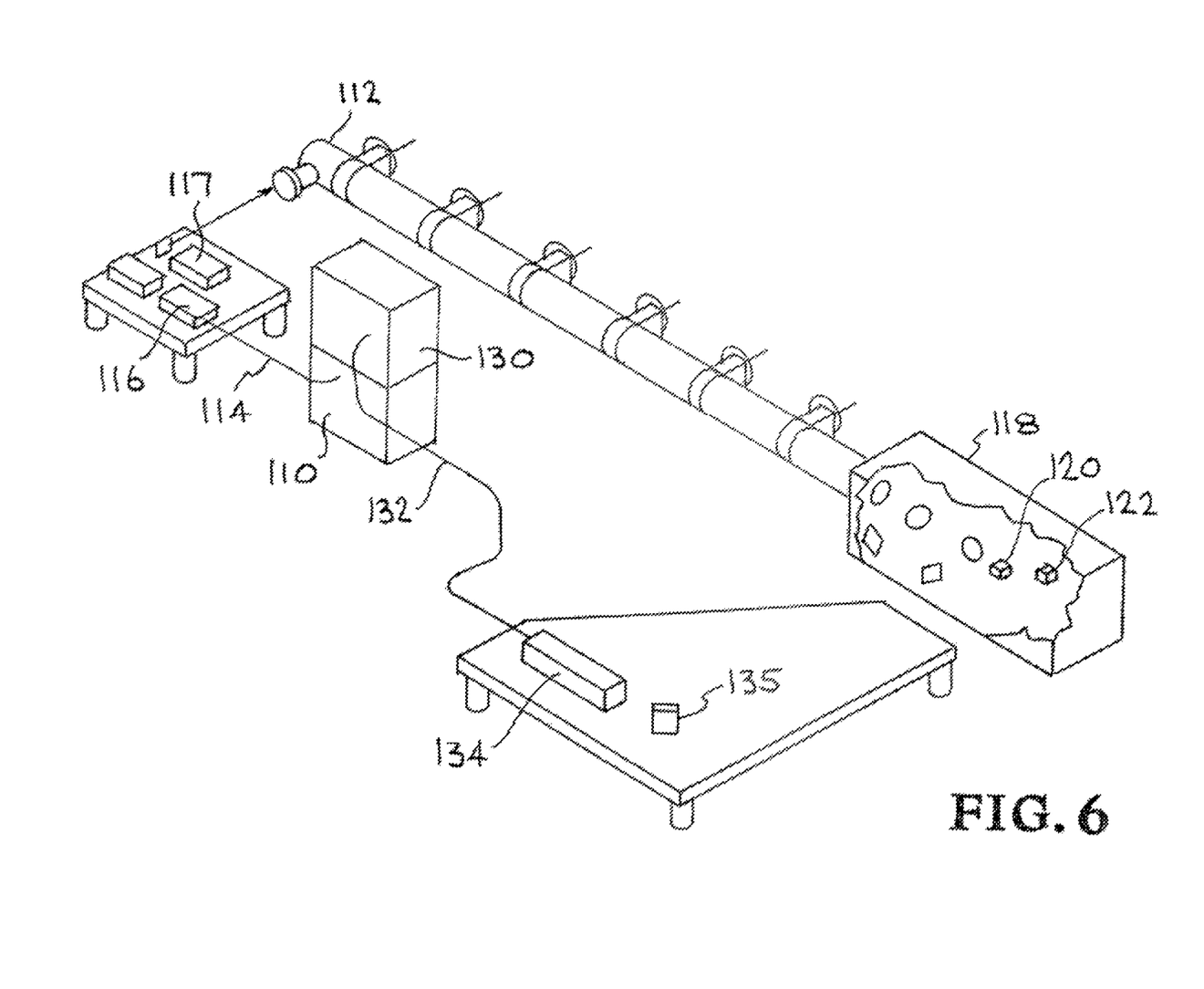
FIG. 6 shows the basic components of an exemplary MEGa-ray source usable in the present invention

FIG. 6 shows the basic components of the exemplary MEGa-ray sources described in U.S. patent application Ser. No. 13/552,610. A laser system in enclosure 110 is configured to drive a photo-gun of a linear accelerator 112. A fiber optic 114 (or other bulk optical arrangement) is provided to transport light from the laser system to an amplifier in enclosure 116. Light from the amplifier is then directed to a frequency conversion means in enclosure 117 to convert the light to an appropriate UV wavelength to drive the photogun. The e-beam output from the linear accelerator 112 is directed into an interaction chamber 118. The interaction chamber includes an interaction region and re-circulating optics and discussed below. An e-beam deflector 120 is provided to direct any residual e-beam toward a beam stop 122.

Referring still to FIG. 1, a laser system in enclosure 130 is configured to provide a long pulse length laser pulse which is directed by a fiber optic 132 (or other bulk optical arrangement) to an amplifier in enclosure 134. The beam from amplifier 134 is directed by mirror 135 through a beam splitter and through a frequency converter (the frequency converter could be omitted and the direct laser beam used if lower energy x-rays or gamma-rays are desired) in interaction chamber 118 and into the oncoming e-beam. The laser beam interacts with the e-beam to produce x-rays or gamma rays.

Exemplary DINO MEGa-ray absorption detectors are briefly described infra and are more specifically described in U.S. patent application Ser. No. 12/506,639, now, U.S. Pat. No. 8,369,480, titled "Dual Isotope Notch Observer for Isotope Identification, Assay and Imaging with Mono-Energetic Gamma-Ray Sources", filed Jul. 21, 2009, incorporated herein by reference.

Figure 7A:
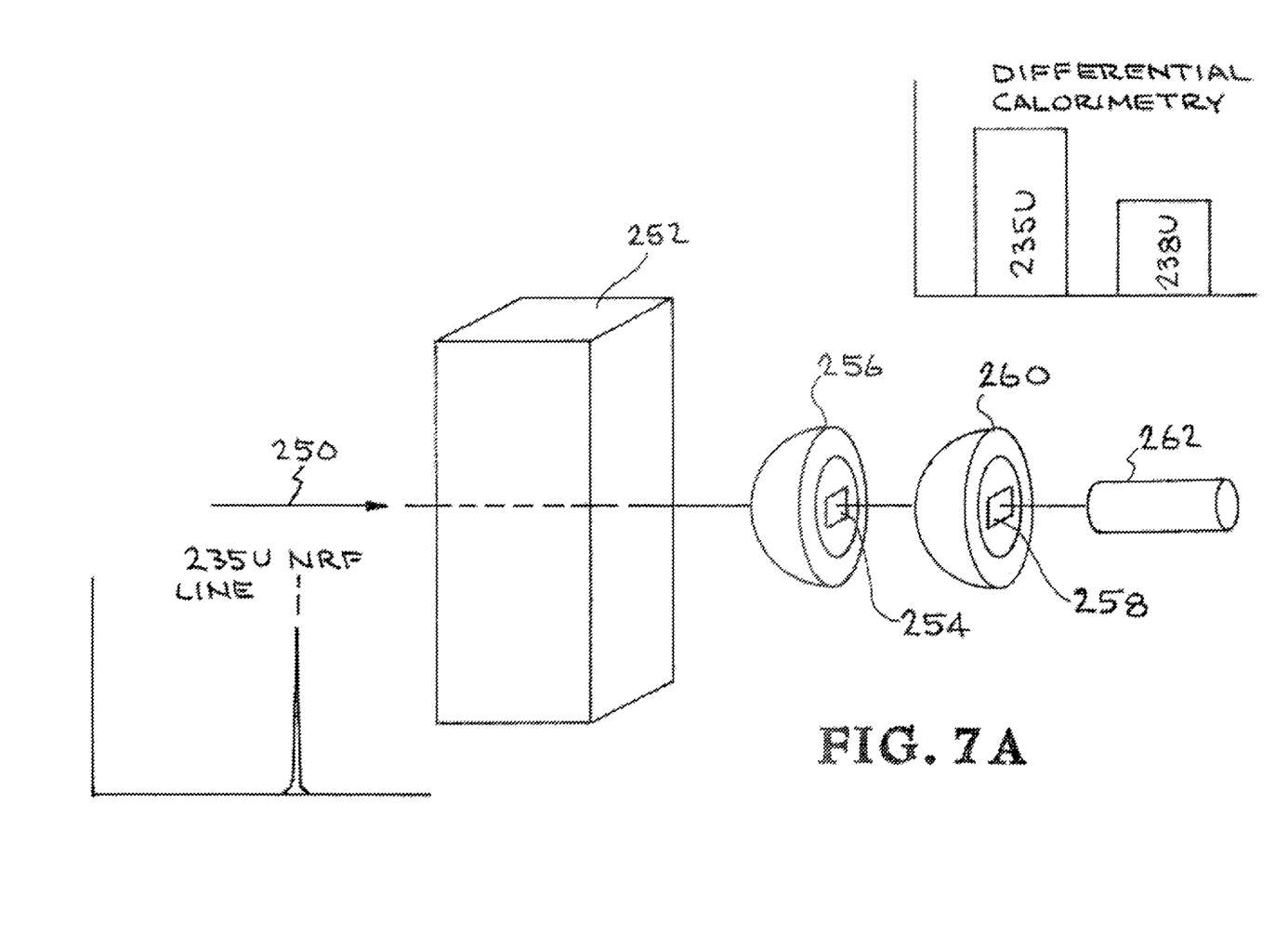
FIG. 7A shows an embodiment of the present invention including a detector arrangement that consists of three detectors downstream from a container having no U235 in the beam path.

FIG. 7A shows an embodiment of the present invention including a detector arrangement that consists of three detectors downstream from a container having no U235 in the beam path.

Figure 7B:
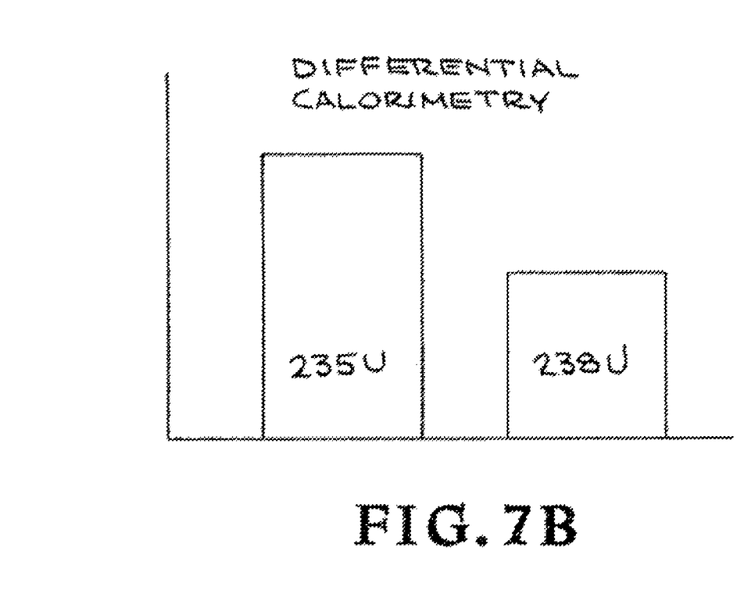
FIG. 7B shows that for an object under interrogation that has no U235 present and the interrogating MEGa-ray beam is tuned to the U235 resonant transition, then the foil will produce resonant photons as well as the non-resonant photons and scatter and thus more energy will emanate from the first foil than the second foil.

FIG. 7B shows that for an object under interrogation that has no U235 present and the interrogating MEGa-ray beam is tuned to the U235 resonant transition, then the foil will produce resonant photons as well as the non-resonant photons and scatter and thus more energy will emanate from the first foil than would if U235 were present in the object under interrogation.

Figure 8A:
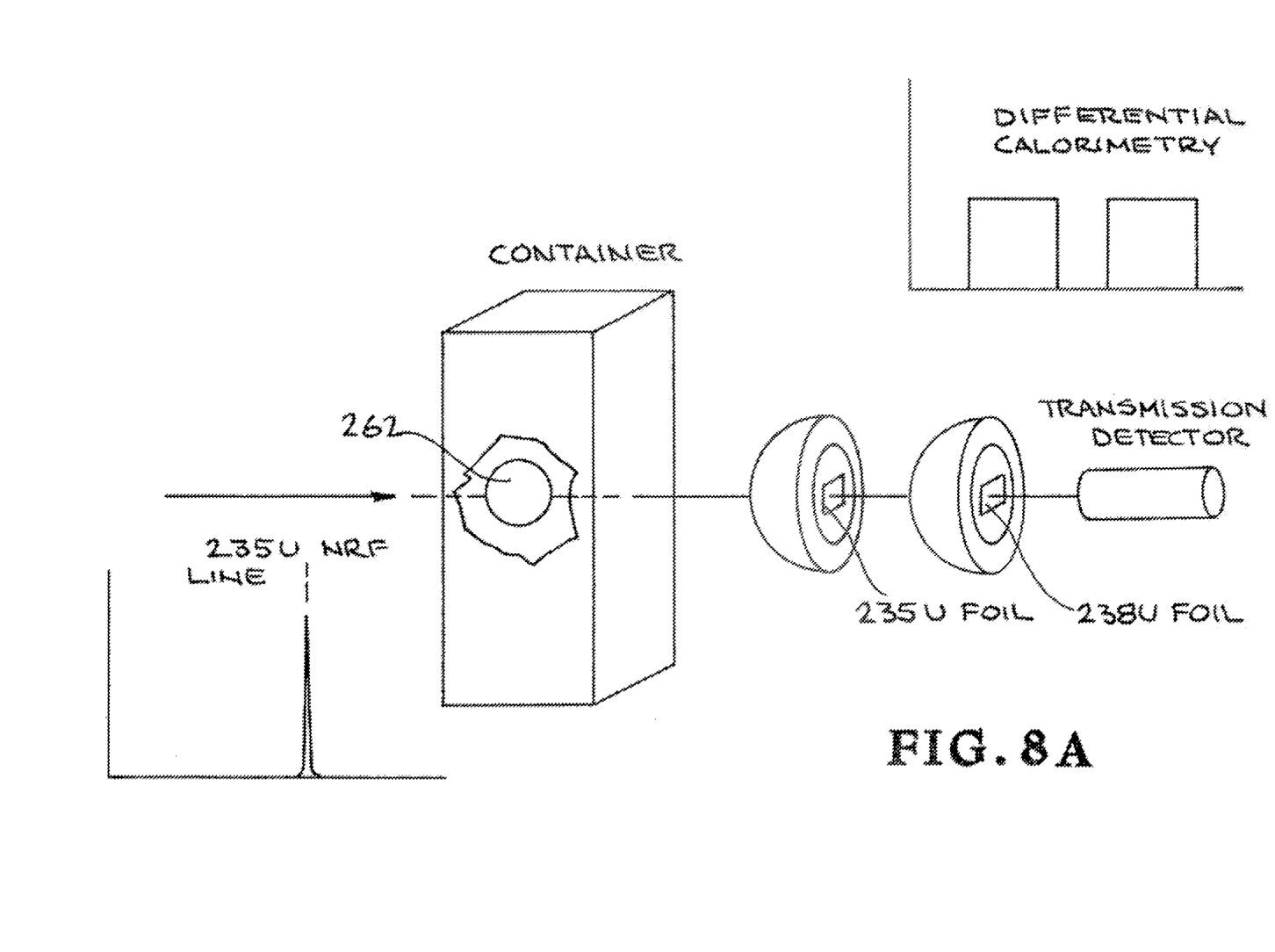
FIG. 8A shows a detector arrangement that consists of three detectors downstream from a container having U235 in the beam path.
Figure 8B:
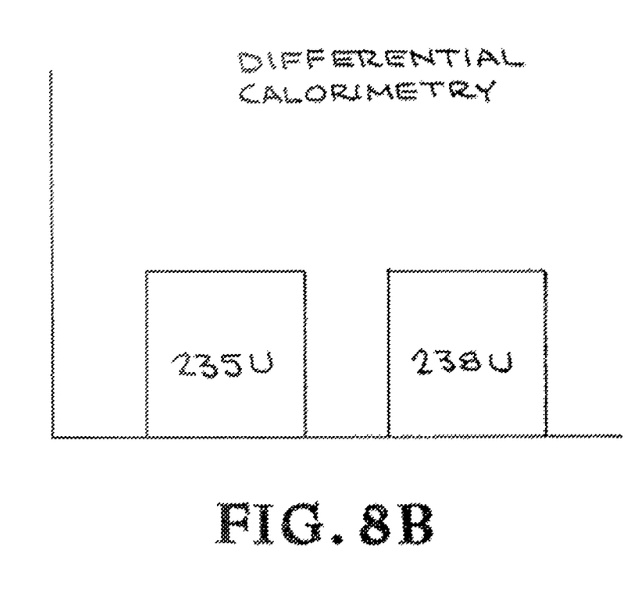
FIG. 8B depicts an example where the amount of U235 is sufficient to remove all of the resonant photons from beam such that there is no production of U235 NRF from the foil.

FIG. 8A shows an embodiment of the present invention including a detector arrangement that consists of three detectors downstream from a container having U235 in the beam path. In this example, the amount of U235 is sufficient to remove all of the resonant photons from beam 250, such that there is no production of U235 NRF from foil 254, as depicted in FIG. 8B.

As discussed above, FIG. 7A shows an example where there is no U235 or U238 in the path of the beam. Specifically, MEGa-ray probe beam 250 is tuned at a U235 NRF line. The path of beam 250 as it traverses container 252, does not intersect any U235 or U238 material. After passing though container 252, beam 250 propagates to and through a first foil 254, which is surrounded by an integrating detector 256. After passing through, foil 254, beam 250 propagates to and through a second foil 258, which is surrounded by an integrating detector 260. After passing through foil 258, beam 250 propagates onto an integrating detector 262. Since beam 250, which is tuned at the U235 NRF line, does not encounter any U235 as it passes through container 252, there is no reduction of U235 resonant photons within beam 250. Therefore, U235 foil 254 produces a larger amount of NRF than it would have if beam 250 had encountered U235 in its path through container 252. If a sufficient quantity of U235 had been present in the path of beam 250 within container 252, such that all of the resonant photons in beam 250 had been removed, then, after normalization of the signals at each detector to account for attenuation losses, the amount of non-resonant photons and scatter from foils 254 and 258 would have, to first order, been the same. In the example of FIG. 8A, there is no U235 (or U238) within the beam path through the container, and therefore, in addition to the non-resonant photons and scattered particles, the integrating detector collects resonance produced by the Interaction of probe beam 250 with the U235 in foil 254. FIG. 8B depicts the signals produced by integrating detectors 256 and 258 in the example of FIG. 8A. The elements of FIG. 9A are identical in all respects to those of FIG. 8A, except that a quantity of U235 material 262 is in the path of beam 250 as it passes through container 252. In this example, the amount of U235 is sufficient to remove all of the resonant photons from beam 250, such that there is no production of U235 NRF from foil 254, as depicted in FIG. 9B. When absolutely no U235 NRF is produced by foil 254, the quantity of U235 within the beam path cannot be surmised. Due to the magnitude of gamma-ray energies (in excess of 1 MeV) produced by the MEGa-ray sources used in the present invention, as disclosed, e.g., in application Ser. No. 11/528,182 (U.S. Pat. No. 7,564,241), incorporated herein by reference, the present invention is capable of producing U235 NRF in foil 254 even in the presence of U235 within the path of team 250 through container 252. Thus, if the amount of U235 NRF produced by foil 254 is less than that produced when beam 250 encounters no U235 in its path through container 254, the amount of U235 that is produced is indicative of the quantity of that material in the path of beam 250. Further, by moving the path of beam 250 relative to container 252, an image, both 2D and 3D, can be obtained of the U235 material within container 252. Other techniques for obtaining a 2D and 3D image are discussed below, and still others will be apparent to those skilled in the art based on the descriptions herein. Although the present invention uses examples for determining the presence, assay and image of U235, the present invention can be used for the same purposes in applications with other materials.

The foregoing description of the invention has been presented for purposes of illustration and description and is not intended to be exhaustive or to limit the invention to the precise form disclosed. Many modifications and variations are possible in light of the above teaching. The embodiments disclosed, were meant only to explain the principles of the invention and its practical application to thereby enable others skilled in the art to best use the invention in various embodiments and with various modifications suited to the particular use contemplated. The scope of the invention is to be defined by the following claims.

We claim:

1. An isotope-specific material flow meter, comprising:
    a mono-energetic x-ray or gamma ray source adapted to produce mono-energetic x-rays or gamma rays of a predetermined energy level which induces nuclear resonance fluorescence (NRF) in a predetermined target isotope;
    a conduit for transporting materials at a predetermined material transport rate to pass and be interrogated by the mono-energetic x-ray or gamma-ray source; and
    a mono-energetic x-ray or gamma ray absorption detection system adapted to measure an attenuation level of the mono-energetic x-ray or gamma ray signal as a function of time and a corresponding amount of the target isotope present in the interrogated material that is passing the source at the material transport rate, wherein said mono-energetic x-ray or gamma ray source comprises:
    an electron source for generating a train of spaced electron bunches;

a radio frequency (RF) linear accelerator for accelerating said electron bunches into a laser-electron beam interaction region to produce accelerated electron bunches, wherein the transit time of each electron bunch of said accelerated electron bunches through said laser-electron beam interaction region is both greater than the duration of said each electron bunch and greater than the spacing between said spaced electron bunches; and a laser system for producing a laser pulse having a duration at least as long as a transit time of said laser pulse through said laser-electron beam interaction region, wherein said laser system is arranged so that said laser pulse traverses said laser-electron beam interaction region to interact with all of said accelerated electron bunches and thereby produce said mono-energetic x-rays or gamma-rays.

2. The flow meter of claim 1, wherein said duration of said laser pulse is substantially equal to at least a total length of said train of spaced electron bunches so that a single pass of said laser pulse through the laser-electron beam interaction region interacts with all of the accelerated electron bunches of said train.

3. The flow meter of claim 1, wherein said duration of said laser pulse is substantially equal to a sub-multiple of a total length of said train of spaced electron bunches and said laser system is arranged to recirculate said laser pulse through said laser-electron beam interaction region for a predetermined number of passes equal to an inverse of said sub-multiple.

4. The flow meter of claim 1, wherein the spacing frequency of said electron bunches is the same as or correlated to the RF frequency of said RF linear accelerator so that an electron bunch is present for every cycle of the RF frequency.

5. The flow meter of claim 1, wherein said gamma-rays comprise a fractional bandwidth of 10E-3 or less.

6. The flow meter of claim 1, wherein the detecting system includes a detector a detector comprising:
a first structure;
a first integrating detector operatively positioned to detect a signal A from said first structure;
a second structure; and
a second integrating detector operatively positioned to detect a signal B from said second structure, wherein said first structure and said second structure comprise the same atomic material, wherein said first structure comprises a portion A that consist essentially of a first isotope, wherein said second structure comprises a portion B that consists essentially of a second isotope, wherein said first structure and said second structure are configured to intercept at least some portion of said mono-energetic x-rays or gamma-rays.

7. The flow meter of claim 6, wherein said first structure comprises a first foil and wherein said second structure comprises a second foil.

8. The flow meter of claim 6, wherein said first isotope consists of $U^{235}$ and wherein said second isotope consists of $U^{238}$.

9. The flow meter of claim 6, wherein said first isotope consists of $Pu^{241}$ and wherein said second isotope consists of $Pu^{239}$.

10. A method of measuring the flow rate of a specific isotope, comprising:
providing a beam of mono-energetic x-rays or gamma rays from a source of mono-energetic x-rays or gamma rays, wherein said beam comprises mono-energetic x-rays or gamma rays of a predetermined energy level which induces nuclear resonance fluorescence (NRF) in a predetermined target isotope;
directing said beam from said source onto a mono-energetic x-ray or gamma ray absorption detection system;
transporting materials through said beam to produce transported materials;
interrogating said transported materials with said mono-energetic x-rays or gamma-rays to measure an attenuation level of the mono-energetic x-ray or gamma ray signal as a function of time and a corresponding amount of the target isotope present in the interrogated material that is passing the source at the material transport rate, wherein the step of providing a beam of mono-energetic x-rays or gamma rays comprises:
generating, with an electron source, a train of spaced electron bunches;
accelerating, in a radio frequency (RF) linear accelerator, said electron bunches into a laser-electron beam interaction region to produce accelerated electron bunches, wherein the transit time of each electron bunch of said accelerated electron bunches through said laser-electron beam interaction region is both greater than the duration of said each electron bunch and greater than the spacing between said spaced electron bunches; and
producing, with a laser system, a laser pulse having a duration at least as long as a transit time of said laser pulse through said laser-electron beam interaction region, wherein said laser system is arranged so that said laser pulse traverses said laser-electron beam interaction region to interact with all of said accelerated electron bunches and thereby produce said beam of monoenergetic x-rays or gamma-rays.

11. The method of claim 10, wherein said duration of said laser pulse is substantially equal to at least a total length of said train of spaced electron bunches so that a single pass of said laser pulse through the laser-electron beam interaction region interacts with all of the accelerated electron bunches of said train.

12. The method of claim 10, wherein said duration of said laser pulse is substantially equal to a sub-multiple of a total length of said train of spaced electron bunches and said laser system is arranged to recirculate said laser pulse through said laser-electron beam interaction region for a predetermined number of passes equal to an inverse of said sub-multiple.

13. The method of claim 10, wherein the spacing frequency of said electron bunches is the same as or correlated to the RF frequency of said RF linear accelerator so that an electron bunch is present for every cycle of the RF frequency.

14. The method of claim 10, wherein said gamma-rays comprise a fractional bandwidth of 10E-3 or less.

15. The method of claim 10, further comprising measuring an attenuation level of the mono-energetic x-ray or gamma ray signal as a function of time and a corresponding amount of the target isotope present in the interrogated material that is passing the source at the material transport rate, wherein the step of measuring is carried out with a detector comprising:
a first structure;
a first integrating detector operatively positioned to detect a signal A from said first structure;
a second structure; and
a second integrating detector operatively positioned to detect a signal B from said second structure, wherein said first structure and said second structure comprise the same atomic material, wherein said first structure comprises a portion A that consist essentially of a first isotope, wherein said second structure comprises a portion B that consists essentially of a second isotope, wherein said first structure and said second structure are configured to intercept at least some portion of said beam of monoenergetic x-rays or gamma-rays.

16. The method of claim 15, wherein said, first structure comprises a first foil and wherein said second structure comprises a second foil.

17. The method of claim 15, wherein said first isotope consists of $U^{235}$ and wherein said second isotope consists of $U^{238}$.

18. The method of claim 15, wherein said first isotope consists of $Pu^{241}$ and wherein said second isotope consists of $Pu^{239}$.

* * * * *